(12) United States Patent
Rübeling

(10) Patent No.: US 6,398,553 B1
(45) Date of Patent: Jun. 4, 2002

(54) T-PLATE FOR RELEASABLY FIXING DENTURES

(75) Inventor: Günter Rübeling, Langener Landstr. 173, 27580 Bremerhaven (DE)

(73) Assignee: Gunter Rubeling (DE)

( * ) Notice: Subject to any disclaimer, the term of this patent is extended or adjusted under 35 U.S.C. 154(b) by 0 days.

(21) Appl. No.: 09/539,960

(22) Filed: Mar. 31, 2000

(30) Foreign Application Priority Data

Apr. 1, 1999 (DE) .......................................... 199 15 109

(51) Int. Cl.$^7$ ............................................... A61C 13/12
(52) U.S. Cl. ....................................... 433/182; 433/181
(58) Field of Search ................................ 433/180, 181, 433/182, 183

(56) References Cited

U.S. PATENT DOCUMENTS 4,752,224 A * 6/1988 Poveromo ................... 433/181
4,767,329 A    8/1988 Schiworia et al. .......... 433/181

FOREIGN PATENT DOCUMENTS

| DE | 196 49 969 | 2/1998 |
| DE | 197 29 704 | 10/1998 |
| EP | 196 11 354 | 10/1987 |
| EP | 0 560 183 | 11/1997 |

* cited by examiner

*Primary Examiner*—John J. Wilson
(74) *Attorney, Agent, or Firm*—Altera Law Group LLC.

(57) ABSTRACT

The invention concerns a t-plate for detachable fixing of false teeth components to one another or to the remaining teeth, with a female part that displays a recess, a male part (6) that displays an attachment section (8) that can be brought to engage the recess in the female part and displays a continuous slot (18) that extends at least through the attachment section (8) and divides the latter into two parts (8a, 8b), and a spreading device (22, 24) that spreads the two attachment section parts (8a, 8b) and displays a first spreading means that is arranged in the slot (18) and is situated so as to engage the two attachment section parts (8a, 8b). The special feature of the invention consists in the fact that the spreading device (22, 24) displays at least one additional spreading means (24) arranged in the slot (18) at a distance from the first spreading means (22a).

11 Claims, 1 Drawing Sheet

T-PLATE FOR RELEASABLY FIXING DENTURES

BACKGROUND OF THE INVENTION

The invention concerns a T-plate for detachable fixing of false tooth components to one another or to the remaining teeth, with a female part that displays a recess, a male part that displays an attachment section that can engage the recess in the female part and a continuous slot, which slot extends at least through the attachment section and divides this into two parts, and a spreading device that spreads the two attachment parts and displays a first spreading means arranged in the slot and situated in engagement with both attachment-section parts.

In such a T-plate the spreading means serves to produce a frictional engagement between the male part and the female part by spreading the two attachment-section parts of the male part, which parts are separated by the slot, whereby the male part is fixed to the female part.

Such a T-plate is known from EP 0 239 821 A1, in which the spreading means is formed by a screw with a cone arranged in its shaft region, which screw is insertable into the slot in a manner parallel to the base of the slot and thus in the longitudinal direction of the slot, so that when the screw has been driven in, the cone is located in the central region of the slot.

Disclosed in DE 196 11 354 A1 is a further T-plate that likewise displays a conical screw as a spreading means. In this known T-plate the cone is formed by the head of the screw and the screw extends through the slot transversely to the base of the slot and thus perpendicularly to the slot, and is situated with its free end in a screw engagement with an anchoring element attached to the removable false teeth.

With the known arrangements, it has proved to be disadvantageous that the spreading of the fixing-section parts that are separated and spaced apart by the slot is not parallel over the length of the slot and thus over the length of the fixing section. This leads to a frictional force that is unevenly distributed over the length of the fixing section. That is, with increasing distance from the spreading means the clamping force decreases considerably, which has a negative effect on the clamping characteristics of the fixing section and thus on the reliability of the holding of the male part on the female part.

SUMMARY OF THE INVENTION

It is thus the object of the present invention to increase the reliability of the clamping hold in a T-plate of the type specified in the introduction.

This object is achieved in a T-plate of the type specified in the introduction by the fact that the spreading device displays, in addition to the first spreading means, at least one second spreading means arranged in the slot at a distance from the first spreading means.

By means of the additional arrangement, according to the invention, of least one additional spreading means, an essentially parallel spreading can be realized, and consequently a distinctly more uniform distribution of the frictional force over the length of the attachment section compared to the prior art, so that even at the ends of the slot the frictional force is not significantly less than at the middle of the slot, but rather is approximately equally great. In doing so, the invention makes use of the knowledge that although the attachment-section parts that are separated by the slot must be elastic in order to be spread apart, this elasticity, however, leads in turn to an undesired flexibility of the attachment-section parts, which flexibility is greater the greater is the distance from the spreading means, and precisely this effect is responsible for the undesired reduction of the frictional force. The flexibility that leads to the lessening of the frictional force is henceforth reduced according to the invention through the arrangement of at least one additional spreading means, without the loss thereby of the elasticity of the attachment-section parts, which elasticity is necessary for the spreading of the attachment-section parts and thus for the production of the desired frictional force. Thus, by means of the invention a frictional force is generated that over the entire length of the slot, or rather of the attachment-section parts of the male part, possesses essentially the same, desired strength, whereby a more effective and reliable clamping hold is realized in comparison to the prior art.

Since precisely the ends of the attachment-section parts are especially flexible, the first spreading means is preferably to be arranged at one end of the slot and the second spreading means at the other end of the slot.

Appropriately, the spreading means should be insertable into the ends of the slot.

An embodiment of the invention that is particularly preferable at present is distinguished by the fact that the spreading means are designed in each case as an axially movable cone. Through the use of cones as spreading means, the desired spreading of the attachment-section parts can be realized in an especially easy manner, since with an axial movement of the cones in the direction of their pointed or narrow ends, the cones come to lie against the inner surface section of the slot and with continued movement act as wedges and widen the slot.

Here, the cones are preferably to be pointed in opposite directions and the spreading arrangement to display a coupling device that effects a movement of the two cones in opposite directions.

In a further development of this embodiment, the slot is widened and in each case displays a section forming a hollow space essentially corresponding to the cones, in which space the cones are arranged.

Appropriately, the cones should be insertable into the slot with their narrow ends and at least one end of the slot widened into a section forming a cone-shaped hollow space that essentially corresponds to one of the cones.

An especially simple and thus effective and advantageous construction of the coupling means can be realized through designing the coupling means as a threaded bolt, in which case the desired axial movement of the cones can be effected through turning the threaded bolt. The threaded bolt should display a head that is formed by the first cone, and the second cone should be designed as a nut that can be screwed onto the threaded bolt, whereby the two cones are oriented with their pointed ends towards each other and therefore arranged so as to be correspondingly movable towards each other. In addition, this construction forms an arrangement that is especially easy to operate, since the threaded bolt is inserted with its free end into one end of the slot and at the other end of the slot is arranged the cone-shaped nut, into which the free end of the threaded bolt screws; through the turning in and tightening of the threaded bolt the two cones come into contact with the corresponding inner surfaces of the slot and widen the latter, which leads to the desired parallel spreading of the attachment-section parts and thus to the production of a friction of the attachment-section parts of the male part in the recess of the female part, which friction is essentially uniform over the length of the attachment-section parts. Of course, as an alternative both cones can, for example, be designed as nuts that can be screwed onto the threaded bolt.

Finally, the slot in the attachment-section parts of the male part is to be formed so deep that it not only divides the attachment section, insertable into the female part, of the male part into two parts, but also divides a section of the male part that borders the attachment section. In this region of the male part, and thus outside the attachment section, the spreading means are preferably to be arranged. As a result the attachment-section parts are not so rigid and enable an improved insertion of the male part with the attachment section into the recess in the female part, whereby a possible premature wearing out is avoided and an optimal fit and level of friction are ensured.

Conventionally, an anchoring element is fixed to the male part. Preferably, on the male part a longitudinal ridge can be formed, onto which the anchoring element is pushed. For this purpose the anchoring element is to display a corresponding recess, which the longitudinal ridge engages. In the longitudinal ridge a slot can preferably be formed, which appropriately runs in the longitudinal direction of the longitudinal ridge, whereby an elastic tongue is formed. Appropriately, this elastic tongue is intended as a locking device that can be brought into a catch-like engagement with the anchoring element. For this purpose, the elastic tongue can be provided with a depression in which the catch projection arranged in the anchoring element locks into place. Instead of the catch projection, use can also be made of a pin that is inserted through a corresponding boring in the anchoring element and put by sections against the depression, so that the latter encloses a section of the circumference of the pin. For fixing the elastic tongue after the placing on of the anchoring element, a screw could also be used, which screw is inserted into the longitudinal ridge of the male part, in which case the inner thread required for this is bounded by the tongue, either along the circumference or on the face. At this point it should be mentioned for the sake of completeness that the above described catch-like holder of an anchoring element on the male part forms an independent aspect of the invention.

BRIEF DESCRIPTION OF THE DRAWINGS

In the following a preferred example of embodiment of the invention will be described in detail with the aid of the drawings. They show.

DETAILED DESCRIPTION OF THE INVENTION

Figure 1:
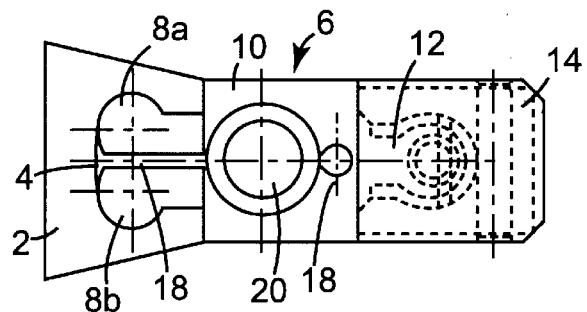
FIG. 1 The face of a T-plate with a female part, a male part attached to the female part, and an anchoring element held onto the male part FIG. 2 a partial sectional side view of the male part of the T-plate of FIG. 1, with spreading screw and spreading nut inserted in the male part, as well as the anchoring element held onto the male part FIG. 3 the male part of FIG. 2 in the same side view, with, however, the spreading screw and spreading nut, as well as the anchoring element, having been omitted
Figure 2:
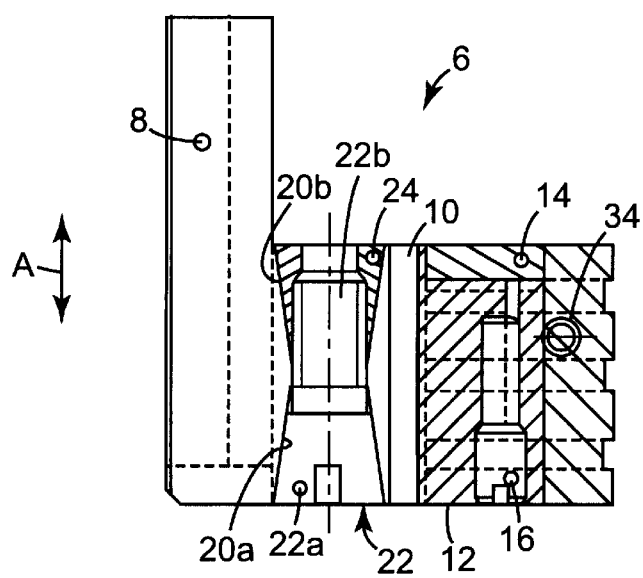

The T-plate represented in the drawings consists of a female part 2, which displays an oblong groove 4, as shown in FIG. 1, as well as a male part 6, which displays a first longitudinal ridge 8, which, for the attachment of the male part 6 to the female part 2, is arranged in the groove 4 of the latter, as can be seen in FIG. 1. For this purpose the groove 4 of the female part 2 and the first longitudinal ridge 8 of the male part 2 essentially correspond in their cross-sectional dimensions, as can likewise be seen in FIG. 1. The male part 6 displays a central section 10, on one long side of which the mentioned first longitudinal ridge 8 is arranged, and on the other, opposite long side of which a second longitudinal ridge 12 is arranged. The second longitudinal ridge 12 serves to hold an anchoring element 14, which in addition can also be fixed to the second longitudinal ridge 12 of the male part 6 by means of a holding screw 16, as FIG. 2 shows.

Formed in the male part 6 is a slot 18 that runs in the longitudinal direction of the first longitudinal ridge 8 according to arrow A (FIG. 2), divides the first longitudinal ridge 8 into two halves 8a and 8b (FIG. 1), which are also called lamellas, and extends from the first longitudinal ridge 8 into the central section 10 of the male part 6 and up to the proximity of the second longitudinal ridge 12, so that the central section 10 of the male part 6 is also divided essentially into two halves by the slot 18. Thus, due to the division by the slot 18 there exist two sections separated from each other and arranged elastically with respect to each other; at their ends it is a matter of lamellas 8a and 8b forming in common the first longitudinal ridge 8. In particular when the male part 6 is produced from metal, a sprung, elastic suspension of the two lamellas 8a and 8b can be realized in an especially effective manner.

Figure 3:
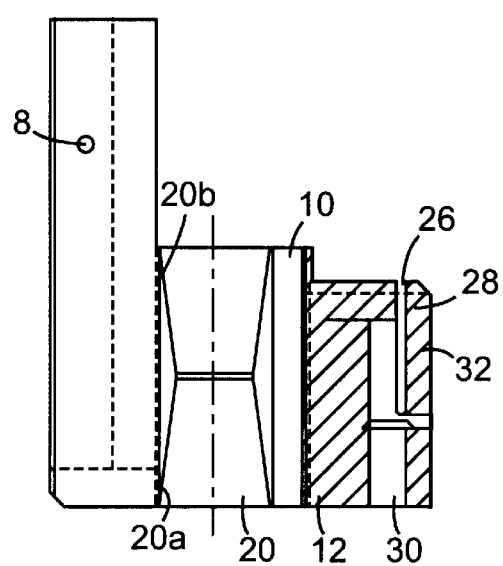

The part of the slot 18 located outside the first longitudinal ridge 8 and inside the central section 10 of the male part 6 is widened into a bore 20, which thus extends in the longitudinal direction through the central section of the male part 6. As can be seen in FIGS. 2 and 3, the bore 20 consists in essence of two cone-shaped section 20a and 20b, each opening towards an end of the bore 20 and thus towards a face of the central section 10 of the male part 6, so that the bore 20 has the form of a double cone (with tips pointed towards each other). It is pointed out here once again that the bore 20 forms a section of the slot 18 and is therefore correspondingly divided by the (rest of) the slot 18.

Inserted into the boring 20 is a spreading screw 22, whose head 22a has the form of a cone that tapers in the direction of the threaded shaft 22b of the screw. The shape of the cone-shaped screw head 22a is adapted to the form of the first cone-shaped section 20a of the bore 20, so that when the spreading screw 22 has been screwed in, its cone-shaped head 22a lies with its circumferential surface essentially in contact with the inner surface of the first cone-shaped section 20a of the bore 20, as shown in FIG. 2. Into the opposite, second cone-shaped section 20b of the bore 20 is inserted a spreading nut 24 that displays a bore with an inner thread, into which the threaded shaft 22b of the spreading screw 22 is screwed, as can likewise be seen in FIG. 2. In the same manner as the cone-shaped screw head 22a, the cone-shaped spreading nut 24 is adapted in its outer shape to the second cone-shaped section 20b of the bore 20, so that after its insertion into the bore 20 the spreading nut 24 lies with its circumferential surface essentially in contact with the inner surface of the second cone-shaped section 20b of the bore 20. In the longitudinal direction the cone-shaped screw head 22a and the cone-shaped spreading nut 24 are dimensioned in such a way that when the spreading screw 22 and the spreading nut 24 have been inserted into the bore 20, neither the screw head 22a nor the spreading nut 24 projects beyond the respective faces of the central section 10 of the male part 6, as shown in FIG. 2, and in addition a space still remains between the screw head 22a and the spreading nut 24, so that for tightening the arrangement of the spreading screw 22 and the spreading nut 24 the spreading screw 22 can be turned still further into the spreading nut 24. Furthermore, the length of the screw shaft 22b of the spreading screw 22 is chosen so that the screw shaft 22b of the spreading screw 22 does not extend completely through the spreading nut 24, but rather ends inside the latter.

During the screwing of the spreading screw into the spreading nut 24 the cone-shaped screw head 22a and the cone-shaped spreading nut 24 come into contact with the cone-shaped sections 20a and 20b of the bore 20. If the spreading screw 22 is then further turned into the spreading nut 24, the cone-shaped screw head 22a and the cone-shaped spreading nut 24 move towards each other along the inner walls of the cone-shaped sections 20a and 20b of the bore 20, whereby radial pressure is exerted on the two halves of the male part 6 separated by the slot 18 and these halves are pressed apart. In this way the lamellas 8a and 8b situated in the groove 4 of the female part 2 are spread and brought into contact with the inner wall of the groove 4. In the process, frictional force is exerted on the inner wall of the groove 4, whereby the male part 6 is attached to the female part 2 through a clamp engagement.

Accordingly, the arrangement formed by the spreading screw 22 and the spreading nut 24 serves as a spreading device that displays two spreading means, consisting of the cone-shaped screw head 22a and the cone-shaped spreading nut 24. Since these two spreading means are spaced apart from each other and exert radial pressure on the two halves of the male part 6 in the sections near the faces of the central section 10 of the male part 6, a parallel spreading of the lamellas 8a and 8a is ensured.

Through the elastic arrangement of the two halves of the male part 6 and in particular of the two lamellas 8a and 8b, upon a turning back of the spreading screw 22 the lamellas 8a and 8b again move towards each other and thus the cone-shaped screw head 22a and the cone-shaped spreading nut 24 come out of contact with the cone-shaped sections 20a and 20b of the bore 20, whereby the clamp engagement of the male part 6 with the female part 2 is undone.

Since the exertion of the radial frictional force for the spreading takes place not in the region of the lamellas 8a and 8b, but rather in the central section 10 of the male part 6, the two lamellas 8a and 8b are always arranged in a slightly springy manner. Accordingly, the lamellas 8a and 8b are not so rigid and for that reason enable an improved insertion into the groove 4 of the female part 2.

In FIG. 3 the structure of the second longitudinal ridge 12 for holding the anchoring element 14 is shown in detail. Formed in the second longitudinal ridge 12 is a longitudinal slot 26, which indeed does not pass completely through, but rather ends beyond the center of the longitudinal ridge 12. Through this longitudinal slot 26 is formed at the free end of the second longitudinal ridge 14 a springy tongue 28. In addition, for taking up the holding screw 16 (FIG. 2) provision is made for a bore 30 with an inner thread, which bore is interrupted by the longitudinal slot 26 in such a manner that the bore is bounded by the springy tongue 28. On the outside the tongue 28 is provided with a transversely-running groove 32.

The anchoring element 14 displays a hollow space (not precisely designated in the figures) that receives the second longitudinal ridge 12 for the attachment of the anchoring element 14 to the male part 6, the anchoring element 14 being pushed over the second longitudinal ridge 12. Here a pin 14, stuck transversely into the anchoring element 34 and extending through the latter's hollow space, engages the groove 32 on the springy tongue 28, so that the pin 34 serves as a catch projection. Of course, other types of catch projections or catch lugs can also be designed and, for example, attached to the inner wall of the hollow space of the anchoring element 14. The engagement of the pin 34 or another catch lug in the groove 32 on the springy tongue 28 gives the technician greater security when fixing the anchoring element 14 to the male part 6.

In addition, the anchoring element 14 is fixed by the holding screw 16, whose shaft also makes contact with the springy tongue 28, as FIG. 2 shows, and thus an undesired bending of the tongue 28 and a detaching of the anchoring element 14 caused by this are prevented.

Finally, it should be mentioned still that the first longitudinal ridge 8, the slot 18, the bore 20, the spreading screw 22, the spreading nut 24, the second longitudinal ridge 12, the holding screw 16, and the longitudinal slot 26 are arranged parallel to one another and extend in the direction of arrow A (FIG. 2).

What is claimed is:

1. T-plate for detachable fixing of false teeth components to one another or to the remaining teeth, comprising a female part having a recess, a male part having an attachment section that can be brought to engage the recess in the female part and having a continuous slot that extends at least through the attachment section and divides the attachment section into two parts, and a spreading device that spreads the two attachment section parts, the spreading device having a first spreading means that is arranged in the slot and is situated so as to engage the two attachment section parts, and at least one additional spreading means arranged in the slot at a distance from the first spreading means.

2. T-plate according to claim 1, wherein the first spreading means is arranged in one end of the slot and the second spreading means in the other end of the slot.

3. T-plate according to claim 1, wherein the spreading means are insertable into the ends of the slot.

4. T-plate according to claim 1, wherein the spreading means are formed in each case as cones that are mounted so as to be axially movable.

5. T-plate according to claim 4, wherein the cones are pointed in opposite directions and the spreading device includes a coupling device that effects a movement of the two cones in opposite directions to each other.

6. T-plate according to claim 5, wherein the coupling means is a threaded bolt.

7. T-plate according to claim 6, wherein the threaded bolt has a head that is formed by the first cone, and that the second cone is a nut that can be screwed onto the threaded bolt.

8. T-plate according to claim 6, wherein both cones are nuts that can be screwed onto the threaded bolt.

9. T-plate according to claim 4, wherein the slot has widened sections that in each case form a hollow space that essentially corresponds to the cones, in which hollow spaces the cones are arranged.

10. T-plate according to claim 9, wherein at least one end of the slot is widened into a section forming a cone-shaped hollow space that essentially corresponds to a cone.

11. T-plate according to claim 4, wherein the cones are insertable into the slot with their narrow ends.

* * * * *